United States Patent [19]
Hell et al.

[11] 3,953,451
[45] Apr. 27, 1976

[54] COMPOUNDS OF THE NAPHTHALIMIDE SERIES
[75] Inventors: Renate Elisabeth Hell, Frankenthal; Horst Scheuermann, Ludwigshafen, both of Germany
[73] Assignee: BASF Aktiengesellschaft, Ludwigshafen (Rhine), Germany
[22] Filed: Nov. 18, 1974
[21] Appl. No.: 524,783

Related U.S. Application Data
[62] Division of Ser. No. 373,114, June 25, 1973, abandoned.

[30] Foreign Application Priority Data
June 28, 1972 Germany............................ 2231609

[52] U.S. Cl..................... 260/281 NH; 260/243 B; 260/247.2 A; 260/268 TR; 260/281 N; 8/1 W
[51] Int. Cl.²................................. C07D 217/24
[58] Field of Search...... 260/281 N, 281 NH, 281 A

[56] References Cited
UNITED STATES PATENTS
3,697,525  10/1972  Okada................................ 260/281

Primary Examiner—R. J. Gallagher
Assistant Examiner—Mark L. Berch
Attorney, Agent, or Firm—Johnston, Keil, Thompson & Shurtleff

[57] ABSTRACT

Naphthalimides of the formula

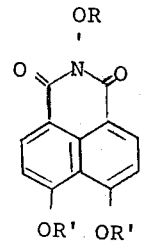

in which R is substituted alkyl or heteroaralkyl and R' is alkyl or alkyl bearing alkoxy or hydroxy as a substituent. The compounds are eminently suitable for the optical brightening of synthetic fibers, particularly acrylonitrile polymers, on which outstanding brightening effects are obtained.

4 Claims, No Drawings

COMPOUNDS OF THE NAPHTHALIMIDE SERIES

This is a division of application Ser. No. 373,114, filed June 25, 1973, now abandoned.

The invention relates to compounds of the formula I

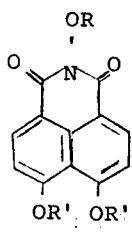

in which

R is -alkylene-T or

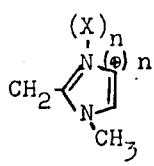

alkene is —CH$_2$CH$_2$—, —CH$_2$CH$_2$CH$_2$—,

—CH$_2$—CH—CH$_3$ or —CH$_2$CH—CH$_2$—
                                  |
                                  OH and

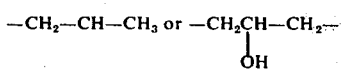

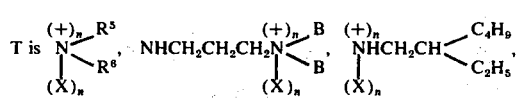

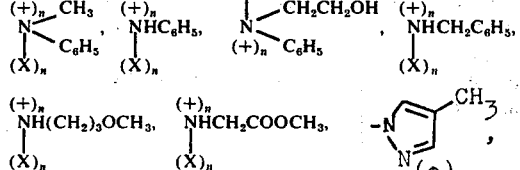

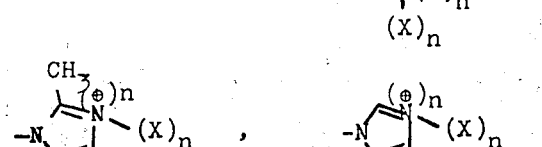

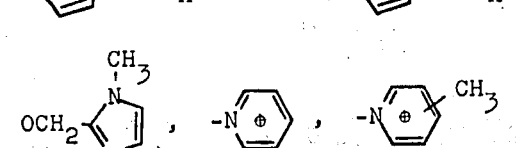

R$^5$ is alkyl of 1 to 4 carbon atoms or β-hydroxyethyl,
R$^6$ is hydrogen, alkyl of 1 to 4 carbon atoms or β-hydroxyethyl, R$^5$ and R$^6$ together with the nitrogen are pyrrolidino, piperidino, morpholino, thiomorpholino dioxide, piperazino, n-methylpiperazino or N-β-hydroxyethylpiperazino, n is 0 or 1, X is methyl, ethyl, propyl or benzyl and R' is alkyl of 1 to 4 carbon atoms, hydroxyalkyl of 2 or 3 carbon atoms or alkoxyalkyl of 2 or 3 carbon atoms in the alkyl and 1 to 4 carbon atoms in the alkoxy group.

Specific examples of R are: γ-dimethylaminopropyl, -diethylaminopropyl and radicals of the formulae:

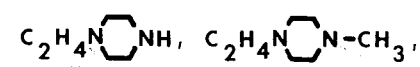

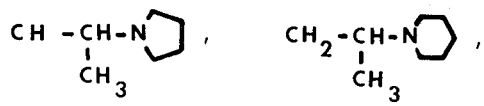

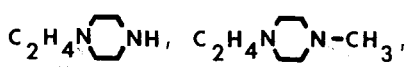

C$_2$H$_4$N(CH$_3$)$_2$, C$_2$H$_4$N(C$_2$H$_5$)$_2$, C$_2$H$_4$N(C$_4$H$_9$)$_2$,

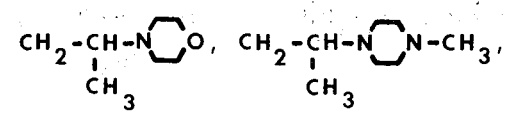

C$_2$H$_4$N(CH$_2$CH$_2$OH)$_2$,

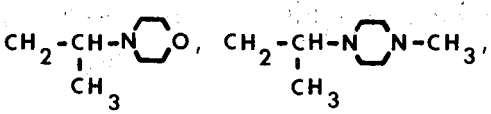

C$_2$H$_4$NHC$_6$H$_5$, C$_2$H$_4$NHCH$_2$C$_6$H$_5$,
C$_2$H$_4$NH(CH$_2$)$_3$N(CH$_3$)$_2$, C$_2$H$_4$NH(CH$_2$)$_3$N(C$_2$H$_5$)$_2$,
C$_2$H$_4$NH(CH$_2$)$_3$N(C$_4$H$_9$)$_2$, C$_2$H$_4$NH(CH$_2$)$_3$OCH$_3$,
C$_2$H$_4$NHCH$_2$COOCH$_3$,

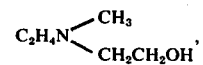

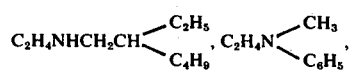

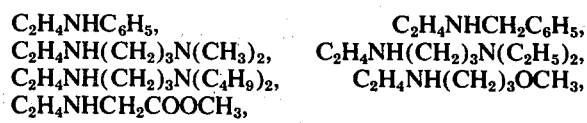

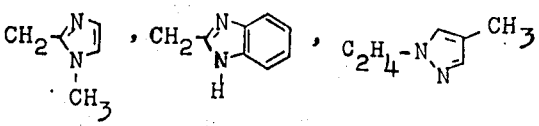

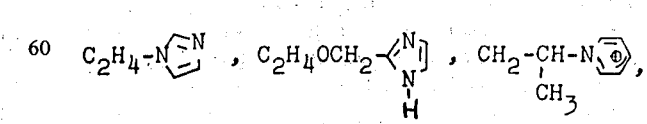

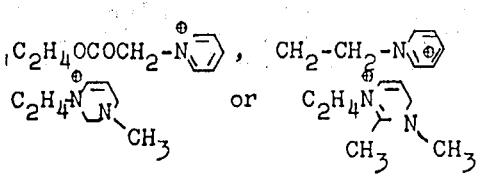

and where $n = 2$ or $3$, $B$ = alkyl of one to four carbon atoms or $C_2H_4OH$, and $X$ = methyl, ethyl, propyl or benzyl:

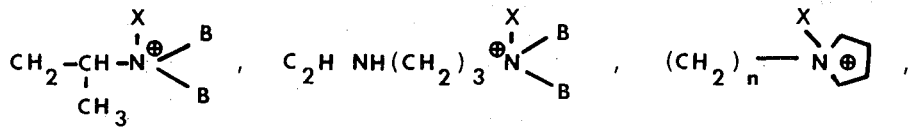

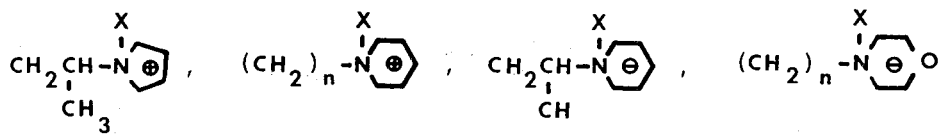

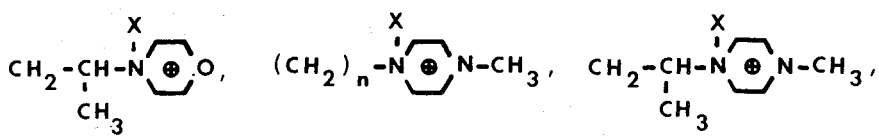

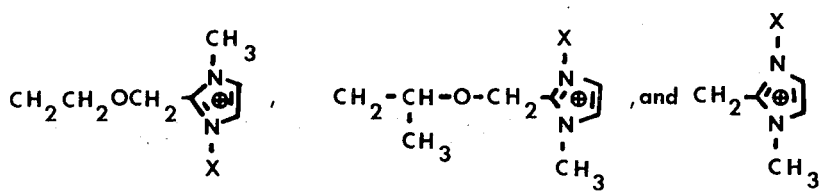

Preferred radicals R are those represented by the formula

- alkylene - T wherein alkylene is $-CH_2CH_2-$, $-CH_2CH_2CH_2-$ or $-CH_2CHCH_3$ and T is

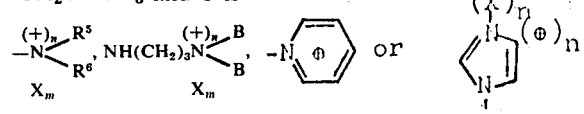

$B$, $n$, $R^5$, $R^6$ and $X$ have the meanings given above.

Examples of suitable counterions (anions) for the ammonium radicals are: chloride, bromide, iodide, sulfate, methosulfate, ethosulfate, benzenesulfonate and toluenesulfonate.

Preferred radicals $R'$ are alkyl of 1 to 4 carbon atoms, hydroxyalkyl of 2 or 3 carbon atoms or alkoxyalkyl of 2 or 3 carbon atoms in the alkyl and 1 to 4 carbon atoms in the alkoxy group. Examples of specific radicals $R'$ are: propyl, butyl, butoxyethyl, ethoxyethyl, methoxyethyl, hydroxyethyl and particularly methyl and ethyl.

It will be understood that references to propyl and butyl include the isomeric radicals such as isopropyl and isobutyl.

Compounds of the formula I may be prepared by the following reactions:

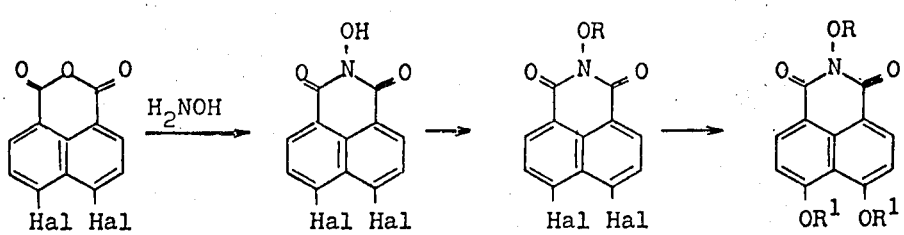

where Hal is bromine or preferably chlorine.

The 4,5-dichloronaphthalic acid anhydride is known from the literature (see e.g. M. M. Daschewski and G. T. Petrenko, Ukranian Chemical Journal, 21, Volume 3 (1955), pages 370 to 721) and is prepared by halogenation and subsequent oxidation from acenaphthene.

Many compounds of the formula (I) may also be prepared by reacting a compound of the formula (II):

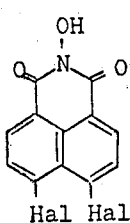

(II)

with an epoxide of the formula (III):

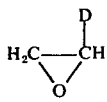

(III)

in which D is hydrogen, methyl or phenyl in an alcohol of the formula:

(in which R' has the above meanings to form a compound of the formula:)

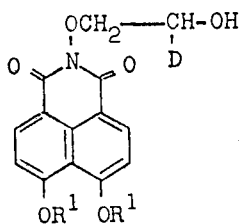

and converting the radical

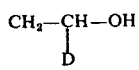

into a radical R.

It is surprising that in the reaction of the compound of the formula (II) with a large (more than 100%) excess of epoxide of the formula (III) in an alcohol of the formula $R^1$—OH often exchange of the halogen for $OR^1$ takes place simultaneously with the introduction of the radical

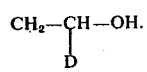

The reactions are known in principle and proceed analogously under comparable conditions. Details are given in the Examples.

The compounds of formula I are colorless to pale yellow and are suitable as optical brighteners, for example, for synthetic fibers such as polyamides, cellulos esters, polyesters and particularly acrylonitrile polymers.

The following Examples illustrate the invention. Parts and percentages are by weight unless otherwise stated.

EXAMPLE 1

28.2 Parts of 4,5-dichloro-N-hydroxynaphthalic acid is dissolved in 1100 parts of methanol and 120 parts of triethylamine with heating under reflux. The solution is filtered, 137.5 parts of β-morpholinoethyl bromide hydrobromide is added and the whole is heated under reflux for three and one half hours. After another 137.5 parts of β-morpholinoethyl bromide hydrobromide has been added, the whole is heated for another hour and the precipitated product is suction filtered and washed with methanol. 4,5-Dichloro-N-β-morpholinoethoxy naphthalimide is obtained.

23.7 Parts of the naphthalimide thus obtained, 43 parts of 30% sodium methylate solution and 250 parts of methanol are heated under reflux for four hours. After the whole has cooled it is suction filtered and washed with methanol and water. 4,5-Dimethoxy-N-β-morpholinoethoxy-naphthalimide is obtained having a melting point of 233° to 234°.

EXAMPLE 2

28.2 Parts of 4,5-dichloro-N-hydroxynaphthalimide is dissolved in 120 parts of triethylamine and 1100 parts of methanol at 60°C. Insoluble matter is filtered off and 22 parts of ethylene oxide is passed in at refluxing temperature. The mixture is heated for another 8 hours, allowed to cool, suction filtered and washed with methanol. 17 Parts (54% of theory) of 4,5-dimethoxy-N-β-hydroxyethoxynaphthalimide is obtained having a melting point of 242° to 243°C. A sample recrystallized from chlorobenzene has the same melting point.

31.7 Parts of 4,5-dimethoxy-N-β-hydroxyethoxynaphthalimide is suspended in 350 parts of chlorobenzene. 0.1 Part of pyridine and 26 parts of phosphorus tribromide are added and the whole is stirred for 5 hours at 25°C. After heating for 6 hours at 110°C the whole is suction filtered and the filter residue is washed with petroleum ether and recrystallized from chlorobenzene. 29 Parts (76% of theory) of 4,5-dimethoxy-N-β-bromoethoxynaphthalimide is obtained as pale yellow crystals having a melting point of 256° to 257°C.

15 Parts of 4,5-dimethoxy-N-β-bromoethoxynaphthalimide and 7 parts of pyridine are added to 50 parts of chlorobenzene and heated for eight hours at 120°C. After cooling the product is suction filtered and stirred for 1 hour in 100 parts of dioxane at 80°C for further purification. 14.5 Parts (80% of theory) of the compound of the formula:

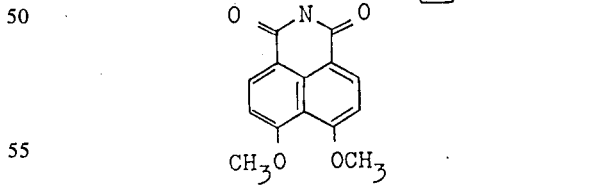

is obtained having a melting point of 213° to 215°C.

The following naphthalimide derivatives are obtained analogously to Example 2:

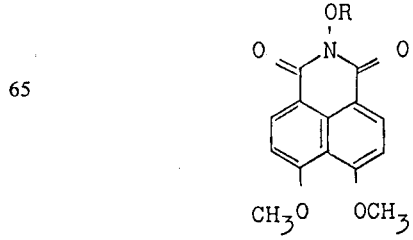

| Example No. | R | | Melting point |
|---|---|---|---|
| 3 | 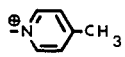 | Br⁻ | 219° to 220°C |
| 4 | 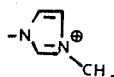 | Br⁻ | 224° to 227°C |
| 5 | 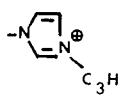 | Br⁻ | 202° to 205°C |

EXAMPLE 6

16 Parts of 4,5-dimethoxy-N-β-hydroxyethoxynaphthalimide is suspended in 160 parts of chlorobenzene and then 12 parts of thionyl chloride and 0.5 parts of dimethylformamide are added. The mixture is stirred for 11 hours under reflux; after cooling, the reaction product is suction filtered and washed with petroleum ether. 16 Parts (96% of theory) of pale yellow crystals is obtained having a melting point of 258° to 259°C. The compound is 4,5-dimethoxy-N-β-chloroethoxynaphthalimide and has the formula:

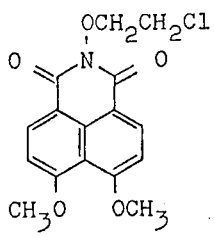

16.8 Parts of 4,5-dimethoxy-N-β-chloroethoxynaphthalimide, 5.3 parts of potassium carbonate, 10 parts of piperidine and 200 parts of chlorobenzene are stirred for 15 hours at 120°C. After cooling, the product is precipitated by adding petroleum ether, suction filtered, stirred with water and recrystallized from propanol. There is obtained 16 parts (83% of theory) of 4,5-dimethoxy-N-β-piperidinoethoxynaphthalimide having a melting point of 205° to 207°C.

EXAMPLE 7

7 Parts of dimethyl sulfate is added to 11.6 parts of 4,5-dimethoxy-N-β-morpholinoethoxynaphthalimide in 100 parts of acetone and the whole is heated for 30 hours under reflux. The product is suction filtered and for further purification is stirred for one hour in 80 parts of dioxane at 70°C. 12 Parts (78% of theory) of the compound of the formula:

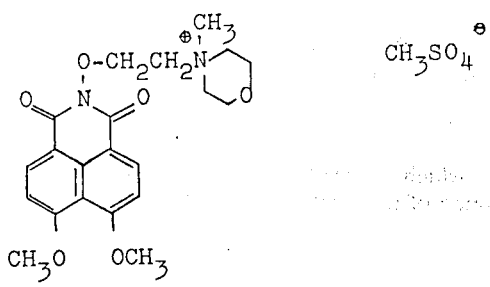

is obtained having a melting point of 220° to 222°C.

Compounds characterized in the following Table by indication of their substituents are obtained by methods analogous to those described in the Examples:

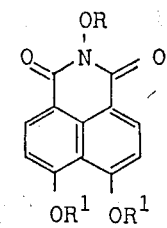

| Example | R | R¹ |
|---|---|---|
| 8 | CH₂CH₂NHCH₂CH₂OH | CH₃ |
| 9 | CH₂CH₂N(CH₃)(CH₃)CH₂CH₂OH ·CH₃ | CH₃ |
| 10 | CH₂CH₂N(C₂H₅)(C₂H₅) | CH₃ |
| 11 | CH₂CH₂N⟨H⟩(cyclohexyl) | C₂H₅ |
| 12 | CH₂CH₂N(CH₂CH₂OH)(phenyl) | CH₃ |

| Example | R | | R¹ |
|---|---|---|---|
| 13 | CH₂CH₂NHCH₃ | | CH₃ |
| 14 | CH₂CH₂NH(CH₂)₃N(CH₃)₂ | | CH₃ |
| 15 |  | | CH₃ |
| 16 | CH₂CH₂NH(CH₂)₃OCH₃ | | CH₃ |
| 17 |  | | CH₃ |
| 18 |  | | CH₃ |
| 19 |  | | CH₃ |
| 20 |  | | CH₃ |
| 21 |  | | CH₃ |
| 22 | 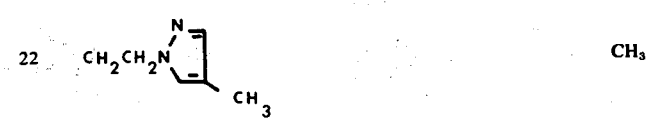 | | CH₃ |
| 23 |  | (ZnCl₄²⁻/2) | CH₃ |
| 24 |  | Br⁻ | CH₃ |
| 25 | 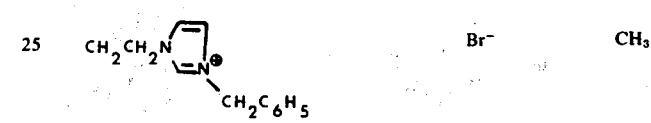 | Br⁻ | CH₃ |

| Example | R | | $R^1$ |
|---|---|---|---|
| 26 |  | Br⁻ | $CH_3$ |
| 27 | $\overset{+}{CH_2CH_2N(C_2H_5)_3}$ | Br⁻ | $CH_3$ |
| 28 |  | $CH_3SO_4^-$ | $CH_3$ |
| 29 |  | $CH_3SO_4^-$ | $CH_3$ |
| 30 |  | $CH_3SO_4^-$ | $CH_3$ |
| 31 |  | $CH_3SO_4^-$ | $CH_3$ |
We claim:
1. A compound of the formula
in which
R is -alkylene-T or
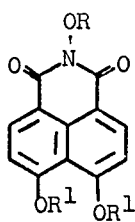
alkylene is —$CH_2CH_2$—, —$CH_2CH_2CH_2$—,
—$CH_2CHCH_3$,
or
—$CH_2CH$—$CH_2$—
$\phantom{-CH_2CH}\overset{|}{OH}$
and
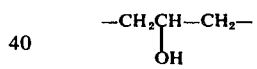
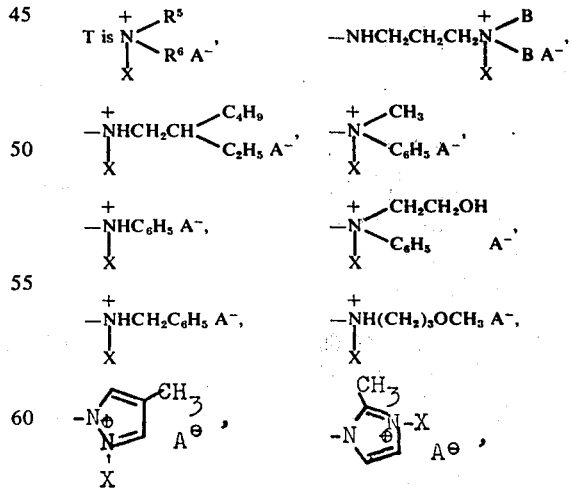
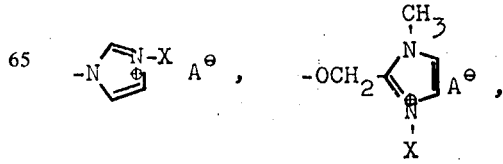

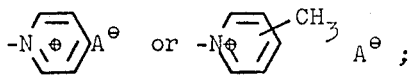

$R^5$ is alkyl of 1 to 4 carbon atoms or β-hydroxyethyl,
$R^6$ is hydrogen, alkyl of 1 to 4 carbon atoms or β-hydroxyethyl,
$R^5$ and $R^6$ together with the nitrogen are pyrrolidino or piperidino,
X is methyl, ethyl, propyl or benzyl,
$R^1$ is $C_1$- to $C_4$-alkyl,
B is $C_1$- to $C_4$-alkyl or $C_2H_4OH$ and
$A^-$ is chloride, bromide, iodide, sulfate, methosulfate, ethosulfate, benzene-sulfonate or toluenesulfonate.

2. A compound according to the formula in claim 1, wherein

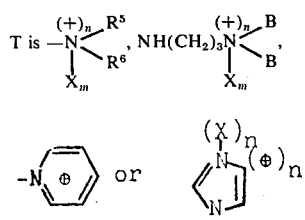

B, $n$, $R^5$, $R^6$ and X having the meanings set forth in claim 1.

3. The compound as claimed in claim 1 of the formula

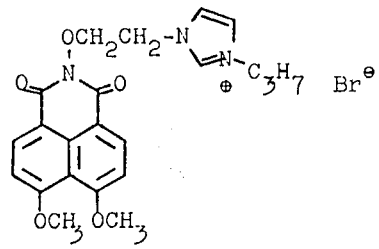

4. The compound as claimed in claim 1 of the formula

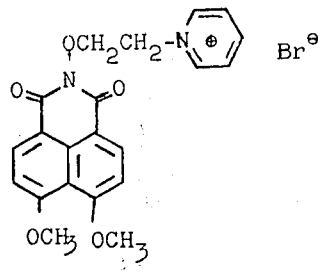

* * * * *